United States Patent [19]

Tsubokura et al.

[11] Patent Number: 5,565,357

[45] Date of Patent: Oct. 15, 1996

[54] PROCESS FOR PRODUCTION OF CANTHAXANTHIN

[75] Inventors: Akira Tsubokura, Kawasaki; Hisashi Yoneda, Yokohama; Mikihiro Takaki, Kawasaki; Takashi Kiyota, Yokohama, all of Japan

[73] Assignee: Nippon Oil Co., Ltd., Tokyo, Japan

[21] Appl. No.: 448,655

[22] Filed: May 24, 1995

Related U.S. Application Data

[62] Division of Ser. No. 258,278, Jun. 10, 1994, Pat. No. 5,496,709.

[30] Foreign Application Priority Data

Jun. 11, 1993 [JP] Japan .................................. 5-140874

[51] Int. Cl.$^6$ ................................ C12N 1/20; C12P 7/26
[52] U.S. Cl. ...................... 435/252.1; 435/67; 435/125; 435/843
[58] Field of Search ................................ 435/252.1, 67, 435/125, 843

[56] References Cited

FOREIGN PATENT DOCUMENTS

454024A2  10/1991  European Pat. Off. ........ C12P 23/00
576870A2   1/1994  European Pat. Off. ......... C12M 1/00
2-138996   5/1990  Japan .............................. C12P 23/00

OTHER PUBLICATIONS

Nelis and DeLeenheer, "Reinvestigation of Brevibacterium sp. Strain KY–4313 as a Source of Canthaxanthin," *Applied and Enviromental Microbiology* 55(10): 2505–2510, 1989.

Xiangmin et al., "Carotenoid pigment in carotenoid producing bacterial cell Cr–1" *Chemical Abstracts 118*: abstract #120571, 1992.

Nelis and DeLeenheer, "Microbial sources of caroentoid pigments used in foods and feeds," *Biotechnology Abstracts: abstract #91–065353, 1991.*

*Primary Examiner*—Herbert J. Lilling
*Attorney, Agent, or Firm*—Seed and Berry LLP

[57] ABSTRACT

A process for production of canthaxanthin comprising the steps of culturing a microorganism capable of producing canthaxanthin and belonging to the genus *Corynebacterium*, such as *Corynebacterium* sp. SQH 348 (FERM BP-4284), and recovering canthaxanthin from the culture.

1 Claim, 3 Drawing Sheets

PROCESS FOR PRODUCTION OF CANTHAXANTHIN

CROSS-REFERENCE TO RELATED APPLICATION

This application is a division of U.S. patent application Ser. No. 08/258,278, filed Jun. 10, 1994, now U.S. Pat. No. 5,496,709.

BACKGROUND OF THE INVENTION

1. Field of the Invention

The present invention relates to a process for production of canthaxanthin which is one of the carotenoid pigments. Canthaxanthin produced by the present process is useful as a natural red pigment in fodder additives, food additives, cosmetics and the like.

2. Related Art

It is known that canthaxanthin is present in a mushroom (Botanical Gazette 112, 228–232, 1950), fishes, and crustaceans (Carotenoids of Aquatic Organisms, Nippon Suisan Gakukai, 1978). In addition as microorganisms producing canthaxanthin, microorganisms belonging to the genus *Brevibacterium* (Applied and Environmental Microbiology, 55(10), 2505, 1989), and microorganisms belonging to the genus *Rhodococcus* (Japanese Unexamined Patent Publication (Kokai) No. 2-138996) are known. Moreover, canthaxanthin can be chemically synthesized by oxidation of β-carotene (J. Amer. Chem. Soc., 78, 1427 (1956)) and synthesis from novel 3-oxo-$C_{15}$ phosphonium salt (Paure Appl. Chem. 51, 875 (1979)).

SUMMARY OF THE INVENTION

The conventional processes, however, have various drawbacks; for example, extraction from natural products is expensive, raw materials are not stably available, productivity by microorganisms is low, and products are accompanied with a lot of impurity. It is problematic to use chemically synthesized canthaxanthin due to safety problems.

The present invention provides a simple process for production of canthaxanthin having high purity and being safe.

The present inventors carried out various attempts to develop a process for production of canthaxanthin using microorganisms. As a result, the present inventors found that microorganisms belonging to the genus *Corynebacterium* accumulate a high concentration of canthaxanthin in their cells, and completed the present invention. The present invention relates to a process for production of canthaxanthin comprising culturing a microorganism having an ability to produce canthaxanthin and belonging to the genus *Corynebacterium*, and extracting and purifying canthaxanthin accumulated in the cells to obtain canthaxanthin.

DETAILED DESCRIPTION

Figure 1:
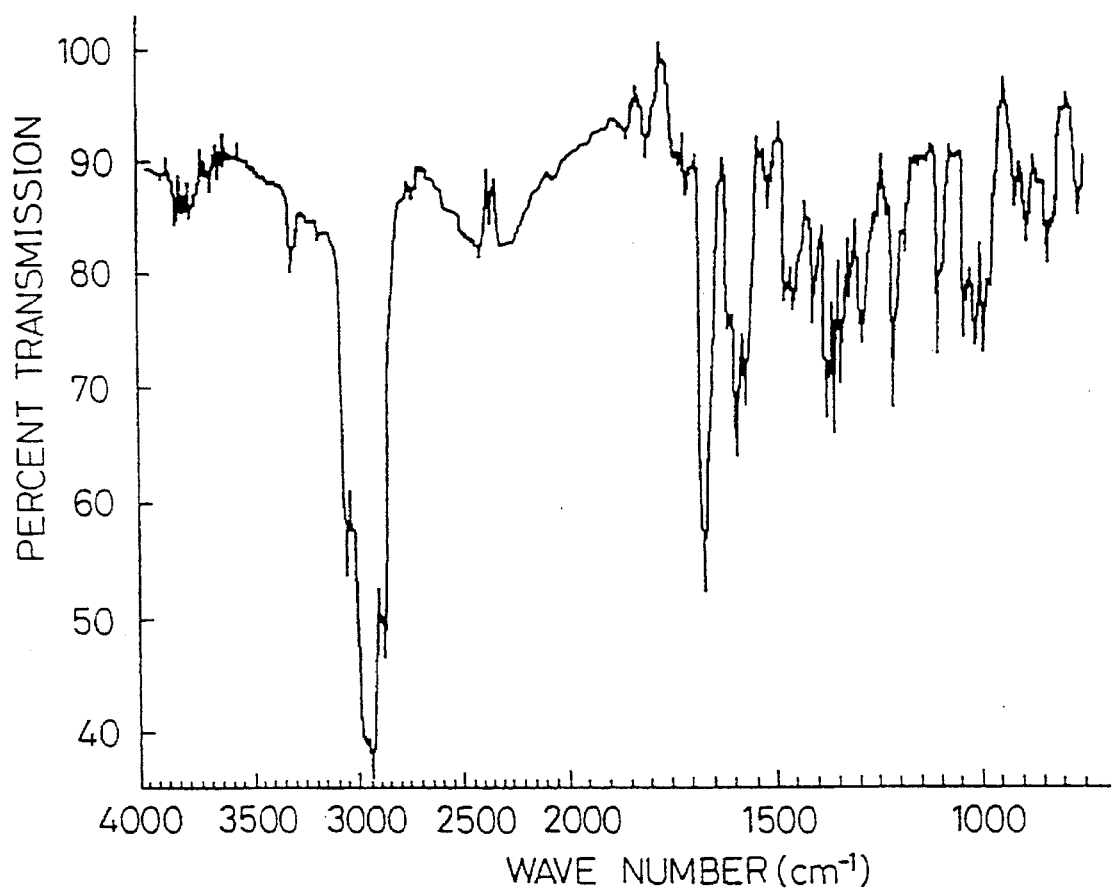
FIG. 1 represents an infrared absorption spectrum of canthaxanthin produced according to the present invention.

According to the present invention, any microorganism belonging to the genus *Corynebacterium* and producing canthaxanthin can be used. As an example, *Corynebacterium* sp. SQH 348 isolated by the present inventors can be mentioned. This strain was deposited to National Institute of Bioscience and Human-Technology, Agency of Industrial Science and Technology, 1—3 Higashi 1-chome, Tsukuba-shi, Ibaraki-ken, 305 Japan, on Apr. 27, 1993 as FERM BP-4284.

This strain has the following taxonomical properties.

| (a) Morphology Bouillon liquid medium | |
|---|---|
| (1) Shape and size of cell | Rod, 0.8 to 1.0 × 1.0 to 1.5 μm |
| (2) Polymorphism | Present |
| (3) Motility | None |
| (4) Spore formation | None |
| (5) Gram stain | Positive |
| (b) Cultural properties on medium | |
| (1) Bouillon agar plate | |
| State of growth | Abundant |
| Color of colony | Orange |
| Shape of colony | Circle (smooth) |
| Gloss of colony | Present |
| Diffusible pigment | None |
| (c) Physiological properties | |
| (1) Reduction of nitrate | − |
| (2) Oxidase | − |
| (3) Catalase | + |
| (4) Range for growth | |
| Growth at pH 6.0 | − |
| Growth at pH 7.0 | + |
| Growth at pH 12.0 | + |
| (5) Behavior toward oxygen | aerobic |
| (6) Liquefaction of gelatin | − |
| (7) Decomposition of esculin | − |
| (8) Decomposition of hippuric acid | − |
| (9) Decomposition of casein | − |
| (10) Decomposition of urea | + |
| (11) Methyl red test | − |
| (12) Glycolate test | − |
| (13) Diamino acid of cell wall | (acetyl type) meso-diaminopimelic acid |
| (14) Sugar composition of cell wall | |
| Arabinose | + |
| Galactose | + |
| (15) Quinone type | MK-8 ($H_2$) |
| (16) GC content | 69 mol % |
| (17) Formation of acid from carbohydrates | |
| (1) Arabinose | − |
| (2) Galactose | − |
| (3) Xylose | − |
| (4) Glucose | − |
| (5) Salicin | − |
| (6) Sucrose | − |
| (7) Starch | − |
| (8) Dextrin | − |
| (9) Trehalose | − |
| (10) Fructose | − |
| (11) Maltose | − |
| (12) Mannose | − |
| (13) Lactose | − |
| (14) Raffinose | − |
| (15) Rhamnose | − |

As a result, the SQH 348 strain was identified as a microorganism belonging to the genus *Corynebacterium* and designated as *Corynebacterium* sp. SQH 348.

According to the present invention, microorganisms other than the strain SQH 348 can be used. Microorganisms which can be used in the present invention can be selected from microorganisms belonging to the genus *Corynebacterium*. For example, microorganisms belonging to *Corynebacterium* are obtained from depository institutes such as ATCC, NRRL, FRI etc. Next they are cultured in a medium such as that described in Table 1, and inoculated into a production medium such as that described in Example 1, and the culture is assayed for canthaxanthin according to the procedure described in Example 1. Microorganisms which produce canthaxanthin are selected and used for the present invention.

Medium for production of canthaxanthin using the present microorganisms is, for example, as follows. Namely, it contains a carbon source, a nitrogen source and inorganic salts necessary for the growth of producer microorganisms, as well as if necessary specially required substances (for example, vitamins, amino acids, nucleic acids etc.). As the carbon sources, sugars such as glucose, fructose, trehalose, mannose, etc., organic acids such as acetic acid, fumaric acid, citric acid, propionic acid, malic acid, malonic acid; alcohols such as ethanol, propanol, butanol, pentanol, hexanol, isobutanol; hydrocarbons such as linear hydrocarbons having 11 to 20 carbon atoms; branched hydrocarbons such as squalene; oil or fat such as rape oil, soybean oil, olive oil, corn oil, linseed oil, and the like are mentioned. Amount of the carbon source added varies according to the kind of the carbon source, and usually 1 to 100 g, preferably 2 to 50 g per 1 l medium.

As the nitrogen sourses, for example, potassium nitrate, ammonium nitrate, ammonium chloride, ammonium sulfate, ammonium phosphate, ammonia, urea, etc. are used alone or in combination. Amount of the nitrogen source added varies according to the kind of the nitrogen source, and usually 0.1 to 10 g, and preferably 1 to 3 g per 1 l medium.

As the inorganic salts, potassium dihydrogen phosphate, dipotassium hydrogen phosphate, disodium hydrogen phosphate, magnesium sulfate, magnesium chloride, ferric sulfate, ferrous sulfate, ferric chloride, ferrous chloride, calcium chloride, calcium carbonate, sodium carbonate, etc. may be used alone or in combination. Amount of inorganic acid varies according to the kind of the inorganic salt, and usually 0.001 to 10 g per 1 l medium.

As special required substances, vitamins, nucleic acids, yeast extract, peptone, meat extract, malt extract, corn steep liquor, dried yeast, etc. may be used alone or in combination. Amount of the special required substance used varies according to the kind of the substance, and usually 0.2 g to 200 g, and preferably 3 to 100 g per 1 l medium. A pH value of a medium is adjusted to pH 2 to 12, preferably 6 to 10. Culturing is carried out a temperature of 15° to 80° C., and preferably 25° to 40° C., usually for 1 to 20 days, and preferably 2 to 8 days, under an aerobic condition provided by shaking or aeration/agitation.

Finally the present compound is isolated and purified from the culture. Namely, microbial cells are separated from the culture by a conventional means such as centrifugation or filtration, and the cells are subjected to an extraction with a solvent. As a solvent for the extraction, any substance in which the present compound is soluble can be used. For example, organic solvents such as acetone, chloroform, dichloromethane, hexane, cyclohexane, ethanol, benzene, carbon disulfide, diethyl ether are used, and preferably chloroform, dichloromethane, acetone or ethanol is used. The purification can be carried out by conventional procedures such as absorption, elution, dissolving and the like, alone or preferably in combination.

Canthaxanthin produced by a microorganism of the present invention is characterized by that it contains a high ratio of all-trans canthaxanthin; a ratio of all-trans:cis is 95:5 to 98:2. The all-trans canthaxanthin is natural type product, and the present microorganisms are advantageous in that they produce the natural type canthaxanthin. If necessary, the cis type canthaxanthin can be synthesized from the all-trans type canthaxanthin, while the all-trans type canthaxanthin cannot be prepared from the cis type canthaxanthin.

The present producer microorganisms are characterized in that they produce canthaxanthin in a wide range of pH value. Namely, they can produce canthaxanthin under an alkaline side pH condition (pH 7 to 10), and are therefore suitable for the production of canthaxanthin which is instable under an acidic condition.

Figure 2:
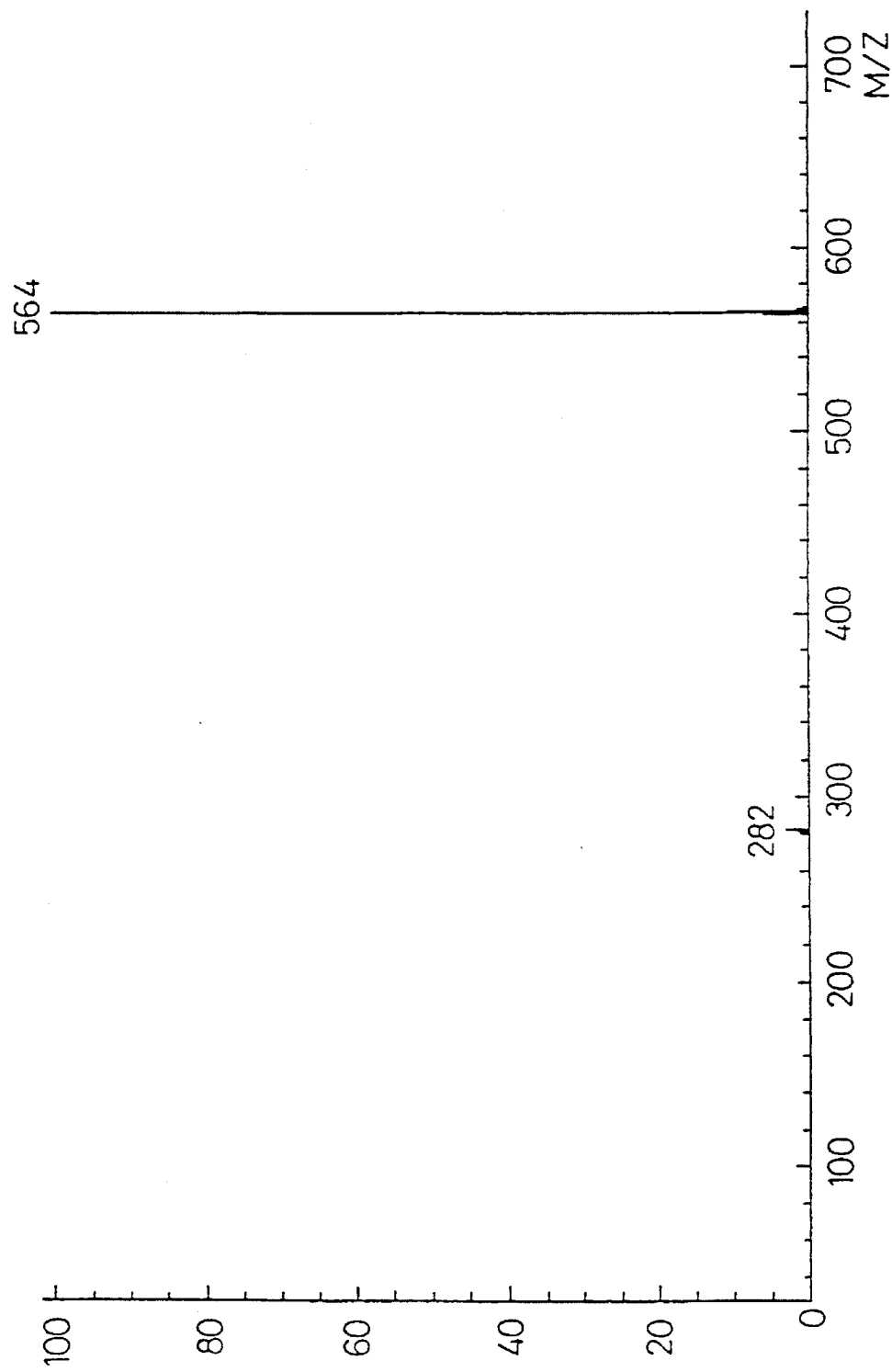
FIG. 2 represents a result of mass analysis of canthaxanthin produced according to the present invention.
Figure 3:
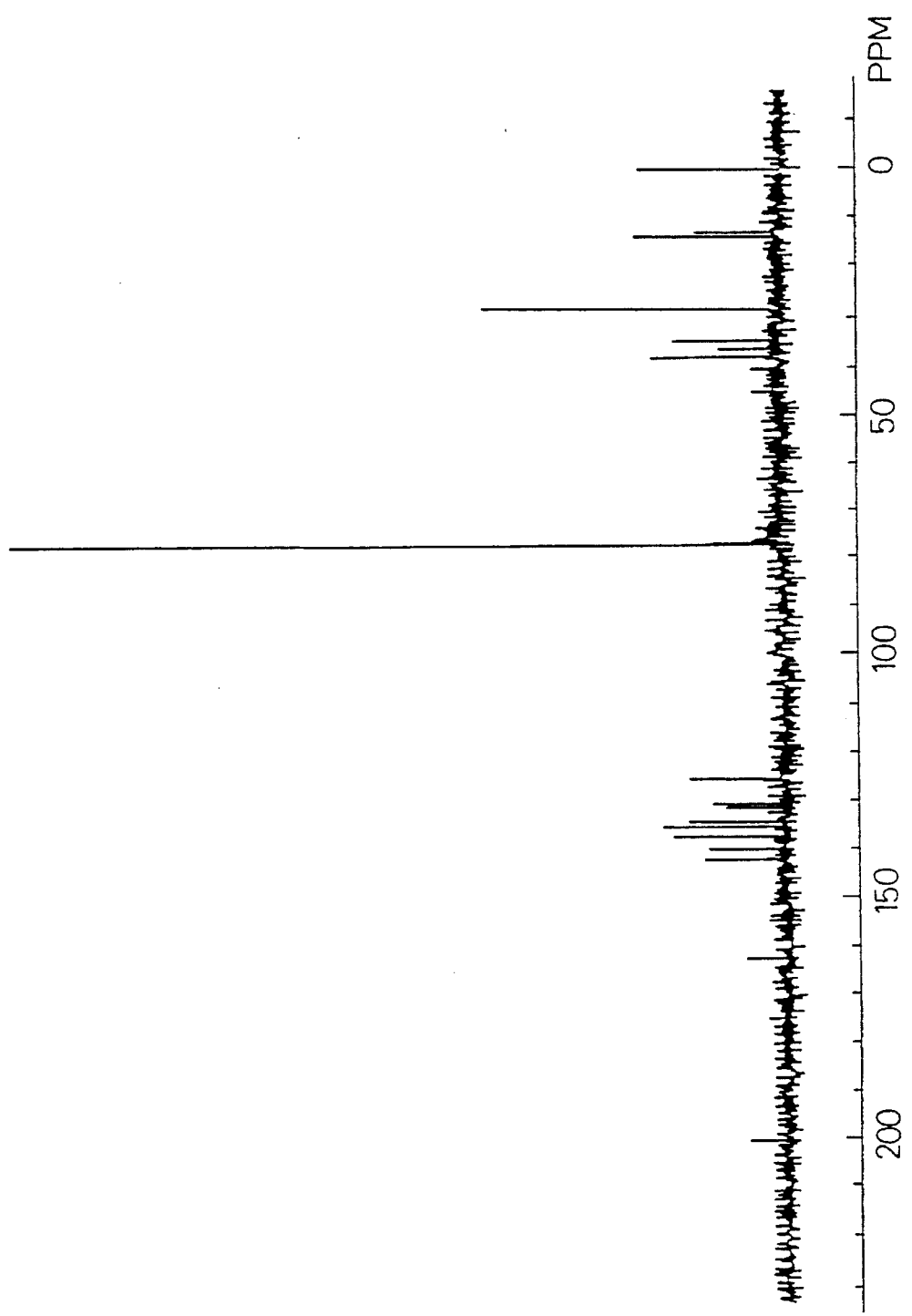
FIG. 3 represents a $^{13}C$ nuclear magnetic resonance of canthaxanthin produced according to the present invention.

An infrared absorption spectrum of canthaxanthin produced according to the present invention is shown in FIG. 1, a mass spectrum thereof is shown in FIG. 2, and $^{13}C$ nuclear resonance spectrum thereof is shown in FIG. 3.

EXAMPLES

Now, the present invention is explained in detail by Examples, but the scope of the present invention should not be restricted to the Examples.

Example 1

First, 10 ml of a medium having a composition shown in Table 1 was put into a test tube having a diameter of 18 mm, and was autoclaved at 121° C. for 15 minutes.

TABLE 1

| | |
|---|---|
| Glucose | 10 g/L |
| Polypepton | 5 g/L |
| Yeast extract | 5 g/L |
| $KH_2PO_4$ | 1 g/L |
| $MgSO_4.7H_2O$ | 0.2 g/L |
| pH 8.0 (adjusted with $Na_2CO_3$) | |

Said medium was inoculated with a piece of cells of SQH 348 strain (FERM BP-4284), and culturing was carried out at 30° C. for 3 days with shaking to prepare an inoculum culture. The inoculum culture was inoculated into a production medium in an amount of 2% by weight inoculum per 100% by weight of the production medium, and culturing was carried out at 30° C. for 8 days with shaking. 50 ml of the production medium was contained in a 500 ml volume Sakaguchi flask, and the production medium contained 2 g/l of a carbon source selected from the group consisting of glucuse, fructose, ethanol, propanol, butanol, and squalene, as well as the components shown in Table 2.

TABLE 2

| Component | Amount |
|---|---|
| Yeast extract | 0.2 g/L |
| $NH_4NO_3$ | 2.5 g/L |
| $KH_2PO_4$ | 1.5 g/L |
| $Na_2HPO_4$ | 1.5 g/L |
| $MgSO_4.7H_2O$ | 0.5 g/L |
| $FeSO_4.7H_2O$ | 0.01 g/L |
| $CaCl_2.2H_2O$ | 0.01 g/L |
| pH 8.0 (adjusted with $Na_2CO_3$) | |

The cultured medium was centrifuged to obtain microbial cells, and the cells obtained from 10 ml of the cultured medium was extracted with 10 ml of acetone, and 10 ml of hexane and 10 ml of 0.85% Sodium Chloride were added to the extract, and the mixture was stirred. The upper layer was separated and the solvent was distilled off at 35° C. under a reduced pressure. An amount of canthaxanthin in the pigment extract was analysed by high performance liquid chromatography. A result is shown in Table 3. The method for analysis by high performance liquid chromatography is described in Applied and Environmental Microbiology, 55 (12), p 3065 (1989). Namely, a ZORBAX ODS (Du pont, 4.6 mm I.D.×250 mm column) was used, and elution was carried out with a mixed solvent of methanol/acetonitrile/dichloromethane (5:4:1). Canthaxanthin was detected by absorption at 470 nm, and quantitated from a ratio of the peak areas for a sample tested and a standard canthaxanthin in a high performance liquid chromatography. In addition, a ratio of canthaxanthin among the other pigments was calculated from a ratio of an area of a peak of canthaxanthin and a total area of peaks of other pigments. In addition, a ratio of all-trans:cis of the canthaxanthin isomers was calculated from a ratio of areas of peaks of the isomers.

TABLE 3

| Carbon source | Canthaxanthin produced (mg/L) | Ratio of canthaxanthin in pigments (%) | Ratio of all-trans: cis |
| --- | --- | --- | --- |
| Glucose | 0.34 | 98.5 | 96:4 |
| Fructose | 0.32 | 99.0 | 96:4 |
| Ethanol | 0.57 | 98.9 | 96:4 |
| Propanol | 0.64 | 99.0 | 96:4 |
| Butanol | 0.48 | 98.9 | 96:4 |
| Squalene | 0.21 | 99.0 | 96:4 |

Example 2

First, 10 ml of a medium having a composition shown in Table 1 was put into a test tube having a diameter of 18 mm, and autoclaved at 121° C. for 15 minutes. The medium was inoculated with a piece of cells of SQH 348 strain (FERM BP-4284), and culturing was carried out at 30° C. for 3 days with shaking to prepare a inoculum culture. The inoculum culture was inoculated into a production medium in an amount of 2% by weight inoculum culture per 100% by weight of the production medium, and culturing was carried out at 30° C. for 5 days with shaking. 50 ml of the production medium was included in a 500 ml volume Sakaguchi flask, and the production medium contained 10 g/l of a carbon source selected from the group consisting of rape oil, olive oil, corn oil, linseed oil and soybean oil as well as the component shown in Table 1. An extraction and quantification of canthaxanthin were carried out as described in Example 1. A result is shown in Table 4.

TABLE 4

| Plant oil | Canthaxanthin produced (mg/L) |
| --- | --- |
| Rape oil | 3.9 |
| Olive oil | 4.5 |
| Corn oil | 4.8 |
| Linseed oil | 1.6 |
| Soybean oil | 5.7 |

Example 3

First, 10 ml of a medium having a composition shown in Table 1 was put into a test tube having a diameter of 18 mm,
and autoclaved at 121° C. for 15 minutes. The medium was inoculated with a piece of cells of SQH 348 strain (FERM BP-4284), and culturing was carried out at 30° C. for 3 days to prepare an inoculum culture. The inoculum culture was inoculated into a production medium in an amount of 2% by weight per 100% by weight of the production medium, and culturing was carried out at 30° C. for 7 days with shaking. 50 ml of the production medium was included in a 500 ml valve Sakaguchi flask. The production medium had a composition shown in Table 2, except that it further contained 10 g/l glucose, 30 g/l yeast extract and 5 ml/l soybean oil, but did not contain $NH_4NO_3$. Extraction and quantification of canthaxanthin were carried out according to the same procedure as described in Example 1. Amount of canthaxanthin produced was 14.1 mg/l.

Example 4

First, 10 ml of a medium having a composition shown in Table 1 was put into a test tube having a diameter of 18 mm, and autoclaved at 121° C. for 15 minutes. The pH value of the medium was adjusted to pH 10.0 with a sterilized 20% $Na_2CO_3$ aqueous solution, inoculated with a piece of cells of SQH 348 strain (FERM BP-4284), and culturing was carried out at 30° C. for 3 days to prepare a inoculum culture. The inoculum culture was inoculated into a production medium in an amount of 2% by weight inoculum culture per 100% by weight of the production culture, and culturing was carried out at 30° C. for 7 days with shaking. The production medium had a composition shown in Table 1, except that pH value was 10.0. Extraction and quantificaiton of canthaxanthin were carried out according to the same procedure as described in Example 1. Amount of canthaxanthin produced was 0.50 mg/l.

Example 5

First, 200 ml of a medium having a composition shown in Table 1 was put into a one liter Sakaguchi flask, and autoclaved at 121° C. for 15 minutes. The medium was inoculated with SQH 348 strain (FERM BP-4284), and culturing was carried out at 30° C. for 3 days. 2.4 l of this culture was inoculated into 25 l of a production medium in a 50 liter fermenter, having a composition shown in Table 1 except that it further contained 0.3 ml/l of Nissan Disfoam BC-51Y (Nippon Yushi) as a antifoaming agent, and culturing was carried out at 30° C., 300 rpm, 1.0 vvm, for 188 hours.

Extraction and quantification of canthaxanthin were carried out according to the procedure as described in Example 1. Amount of canthaxanthin produced was 2.0 mg/l. 21.4 kg of the culture was centrifuged to obtain 298g of wet cells, which were then homogeneously mixed with 500 ml of chloroform. The mixture was centrifuged to separate and recover the aqueous lower layer. The aqueous layer was extracted twice with chloroform to obtain 1.5 l of an extract containing canthaxanthin. The extract was evaporated off under a reduced pressure, and the concentrated extract containing canthaxanthin was adsorbed on a silica gel column.

Canthaxanthin was eluted with a mixed solvent of hexane/ethyl acetate (9:1), and solvent was evaporated off from the elute. The extract was dissolved in a small amount of chloroform, and ethanol was dropwise added to the solution so as to crystallize canthaxanthin. 7.5 mg of crystallized canthaxanthin was obtained. Canthaxanthin thus obtained was identical with authentic canthaxanthin in an infrared absorption spectrum, mass spectrum, $^{13}C$ nuclear magnetic resonance spectrum and absorption spectrum.

Example 6

First, 100 ml of a medium having a composition shown in Table 1 was put into a 500 ml Sakaguchi flask, and autoclaved at 121° C. for 15 minutes. The medium was inoculated with SQH 348 strain (FERM BP-4284), and culturing was carried out at 30° C. for 3 days to prepare an inoculum culture. 100 ml of the culture was inoculated into 1 l of a medium having a composition shown in Table 1 in a 2.5 l fermenter, and culturing was carried out at 30° C., 500 rpm and 1.0 vvm, for 67 hours. Extraction and quantification of canthaxanthin were carried out according to the same procedure as described in Example 1. Amount of canthaxanthin produced was 3.4 mg/l.

Example 7

First, 100 ml of a medium having a composition shown in Table 1 was put into a 500 ml Sakaguchi flask, and autoclaved at 121° C. for 15 minutes. The medium was inoculated with SQH 348 strain (FERM BP-4284) and culturing was carried out at 30° C. for 3 days with shaking to prepare an inoculum culture. 100 ml of the culture was inoculated into 1 l of a production medium in a 2.5 l fermenter, and culturing was carried out at 30° C., 500 rpm and 1.0 vvm, for 44 hours in an aerobic condition. The production medium has a composition shown in Table 1, except that it contained 10 ml/l of ethanol in place of glucose. Extraction and quantificaiton of canthaxanthin were carried out according to a procedure as described in Example 1. Amount of canthaxanthin produced was 2.4 mg/l.

Example 8

First, 100 ml of a medium having a composition shown in Table 2, except that it contained 20 g/l glucose, 20 g/l yeast extract and 5 g/l of soybean oil but did not contain $NH_4NO_3$, was autoclaved at 121° C. for 15 minutes. The medium was inoculated with SQH 348 strain (FERM BR- 4284) and culturing was carried out at 30° C. for 3 days with shaking to prepare an inoculum culture. 100 ml of the culture was inoculated into 1.25 l of a production medium in a 2.5 l fermenter, and culturing was carried out at 30° C., 500 rpm mand 1.0 vvm, for 163 hours in an aerobic condition. The production medium had a composition shown in Table 2, except that it contained 10 g/l glucose, 30 g/l yeast extract, and 5 ml/l soybean oil and does not added $NH_4NO_3$. During the culturing at 50, 66, 74 and 90 hours from the inoculation, 12 g of glucose was added to maintain the presence of glucose. In addition at 42, 66 and 90 hours from the inoculation, 3 g/l of soybean oil was added. Extraction and quantification of canthaxanthin were carried out according to the same procedure as described in Example 1. Amount of canthaxanthin produced was 19.5 mg/l.

Example 9

First, 100 ml of a medium having a composition shown in Table 2 (except that it contained 20 g/l glucose, 20 g/l yeast extract and 5 g/l soybean oil, but does not contain added $NH_4NO_3$) was put into a 500 ml Sakaguchi flask, and autoclaved at 121° C. for 15 minutes. The medium was inoculated with SQH 348 strain (FERM BP-4284), and culturing was carried out at 30° C. for 3 days to prepare an inoculum culture. 100 ml of this culture was inoculated into 1.2 l of a production medium in a 2.5 liter fermenter, and culturing was carried out at 30° C., 800 rpm and 1.0 vvm, for 141 hours. The production medium had a composition shown in Table 2, except that it contained 10 ml/l ethanol, 30 g/l yeast extract and 5 ml/l soybean oil, but does not contain added $NH_4NO_3$. Total 19 ml of ethanol was periodically added so as to maintain the presence of ethanol. When foam was formed on the medium, soybean oil was fed with a pump cooperating with a foam detecting electrode. Total amount of soybean oil fed was 43 ml. Extraction and quantification of canthaxanthin were carried out according to the same procedure as described in Example 1. Amount of canthaxanthin produced was 13.6 mg/l.

Example 10

First, 100 ml of a medium having a composition shown in Table 1 was put into a 500 ml Sakaguchi flask, and autoclaved at 121° C. for 15 minutes. The medium was inoculated with SQH 348 strain (FERM BP-4284) and culturing was carried out at 30° C. for 3 days to prepare an inoculum culture. 100 ml of the culture was inoculated into 1.2 l of a production medium in a 2.5 liter fermenter, and culturing was carried out at 30° C., 500 rpm and 1.0 vvm for 158 hours. The production culture had a composition shown in Table 1 except that it contained 10 ml/l proponol, 40 g/l yeast extract, and 0.01 ml/l Nissan Disfoam BC-51Y, but did not contain added $NH_4NO_3$. Extraction and quantification of canthaxanthin were carried out according to the same procedure as described in Example 1. Amount of canthaxanthin produced was 7.2 mg/l.

This application claims priority from Japanese Patent Application Serial No. 5-140874, which is incorporated herein by reference in its entirety.

We claim:

1. A microorganism which is an isolated *Cornybacterium* sp. SQH 348 (FERM BP-4284).

* * * * *